United States Patent
Sun et al.

(10) Patent No.: US 7,994,780 B2
(45) Date of Patent: Aug. 9, 2011

(54) SYSTEM AND METHOD FOR INSPECTION OF PARTS WITH AN EDDY CURRENT PROBE

(75) Inventors: Haiyan Sun, Niskayuna, NY (US); Changting Wang, Niskayuna, NY (US); William Stewart McKnight, Hamilton, OH (US)

(73) Assignee: General Electric Company, Niskayuna, NY (US)

(*) Notice: Subject to any disclaimer, the term of this patent is extended or adjusted under 35 U.S.C. 154(b) by 803 days.

(21) Appl. No.: 11/855,816

(22) Filed: Sep. 14, 2007

(65) Prior Publication Data

US 2009/0072822 A1 Mar. 19, 2009

(51) Int. Cl.
*G01N 27/82* (2006.01)

(52) U.S. Cl. .......................... 324/240; 324/242

(58) Field of Classification Search ............... None
See application file for complete search history.

(56) References Cited

U.S. PATENT DOCUMENTS

| | | | | |
|---|---|---|---|---|
| 2,728,217 A * | 12/1955 | Richardson | .................. | 73/25.02 |
| 2,729,103 A * | 1/1956 | Raynsford et al. | ......... | 73/861.16 |
| 2,808,723 A * | 10/1957 | Buntenbach | ............... | 73/861.17 |
| 3,710,236 A * | 1/1973 | Halsey et al. | ................. | 324/235 |
| 3,720,870 A * | 3/1973 | Sueda | ............................ | 324/239 |
| 3,747,085 A * | 7/1973 | Bala et al. | ...................... | 340/680 |
| 4,394,193 A * | 7/1983 | Gfrerer | ......................... | 148/509 |
| 4,441,077 A * | 4/1984 | Dodgen et al. | ................ | 324/164 |
| 4,593,245 A | 6/1986 | Viertl et al. | | |
| 4,594,549 A * | 6/1986 | Smith et al. | .................. | 324/232 |
| 4,875,357 A * | 10/1989 | Giallorenzi | .................... | 356/437 |
| 5,028,869 A * | 7/1991 | Dobmann et al. | ............ | 324/223 |
| 5,262,722 A | 11/1993 | Hedengren et al. | | |
| 5,389,876 A | 2/1995 | Hedengren et al. | | |
| 5,442,286 A * | 8/1995 | Sutton et al. | .................. | 324/242 |
| 5,610,517 A * | 3/1997 | Ma et al. | ....................... | 324/233 |
| 6,046,585 A * | 4/2000 | Simmonds | .................... | 324/239 |
| 6,165,542 A * | 12/2000 | Jaworowski et al. | ........... | 427/10 |
| 6,275,031 B1 * | 8/2001 | Simmonds | .................... | 324/239 |
| 6,437,563 B1 * | 8/2002 | Simmonds et al. | ........... | 324/239 |
| 6,670,808 B2 * | 12/2003 | Nath et al. | .................... | 324/230 |
| 7,206,706 B2 * | 4/2007 | Wang et al. | ..................... | 702/64 |
| 2002/0145416 A1 * | 10/2002 | Attarian et al. | ................ | 324/127 |
| 2003/0038628 A1 | 2/2003 | Nath et al. | | |
| 2006/0202687 A1 * | 9/2006 | Wang et al. | .................... | 324/238 |
| 2006/0217908 A1 * | 9/2006 | Wang et al. | ..................... | 702/64 |
| 2007/0027353 A1 * | 2/2007 | Ghiron et al. | ..................... | 600/9 |
| 2008/0278151 A1 * | 11/2008 | Wang et al. | .................... | 324/219 |

* cited by examiner

*Primary Examiner* — Jay M Patidar
(74) *Attorney, Agent, or Firm* — Scott J. Asmus

(57) ABSTRACT

An inspection system for detecting a flaw in a part is provided. The inspection system includes a generally C-shaped core having an opening for receiving the part. The system also includes a driver coil wrapped around the core for creating a magnetic field in the opening. The system further includes at least one single element or multiple element eddy current sensor disposed in the opening.

20 Claims, 5 Drawing Sheets

SYSTEM AND METHOD FOR INSPECTION OF PARTS WITH AN EDDY CURRENT PROBE

BACKGROUND

The invention relates generally to a system for nondestructive inspection of parts, and more particularly, to a system for detecting flaws in parts employing eddy current techniques.

Coating systems are employed throughout many mechanical parts and systems, such as gas turbine engines. Such coating systems provide protection from elements such as, but not limited to, interference rubs, and high temperatures and so forth in harsh environments in which gas turbine engines operate. Components, such as seal teeth, employ coatings to improve wear and corrosion resistance and extend their useful lives. Moreover, such components undergo stress over a period of time and must be inspected under the coating, periodically to avoid damage to the engine.

There are several widely used nondestructive inspection techniques for detecting flaws in such coating systems. One commonly used technique is a fluorescent penetration inspection (FPI) technique. In the FPI technique, the coating is first removed from a coated part before inspecting a base metal of the part for cracks and flaws. A liquid fluorescent is penetrated into the part that is cleaned and is allowed to adsorb into features such as cracks and other flaws in the part. The part is further exposed to an ultraviolet radiation causing trapped penetrant to fluoresce. The part is recoated after inspection and cleaning.

The FPI technique typically has a limited detection capability with a low probability of detection, and its reliability is highly dependent upon process parameters and experience of an operator in interpreting an indication as a flaw. For example, a flaw indication may be misinterpreted or missed due to background noise. Furthermore, removal of coating before inspection is time consuming, often not economically feasible or quite expensive, and may cause potential damage to the part.

Accordingly, there is a need for an improved inspection technique for detecting flaws in a surface and sub-surface region of coated and uncoated systems.

BRIEF DESCRIPTION

In accordance with one aspect of the invention, an inspection system for detecting a flaw in a part is provided. The system includes a generally C-shaped core having an opening for receiving a part. The system also includes a driver coil wrapped around the core for creating a magnetic field in the opening. The system further includes at least one single element or multiple element eddy current sensor disposed in the opening.

In accordance with another aspect of the invention, an inspection system for detecting a flaw in a part is provided. The system includes a generally C-shaped core having an opening for receiving a part. The system also includes a driver coil wrapped around the core for creating a magnetic field in the opening. The system further includes a single or multiple element eddy current sensors disposed in the opening. A driving circuit is configured to apply a plurality of excitation signals in the driver coil to induce a plurality of eddy current signals in the part. A detection circuit configured to detect the plurality of eddy current signals.

In accordance with another aspect of the invention, a method of inspecting a flaw in a part is provided. The method includes positioning the part in an opening of an inspection system, wherein the inspection system includes a generally C-shaped core having an opening for receiving the part and a driver coil wrapped around the core for creating a magnetic field in the opening. The inspection system also includes a single or multiple element eddy current sensors disposed in the opening. The method also includes energizing the driver coil to induce a plurality of eddy current signals in the part. The plurality of eddy current signals from the sensor are then read.

In accordance with another aspect of the invention, a method of manufacturing an inspection system is provided. The method includes disposing a driver coil around a generally C-shaped core. The method also includes disposing a single or multiple element eddy current sensors inside an opening of the core.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed in detail below, embodiments of the invention include a system and method for inspection of parts by inducing an eddy current. As used herein, the term "inspection" includes inspection for detecting flaws in a surface and a sub-surface region of the parts such as, but not limited to, internal cracks, external cracks and pits. A non-limiting example of the part includes seal teeth in an aircraft engine.

Figure 1:
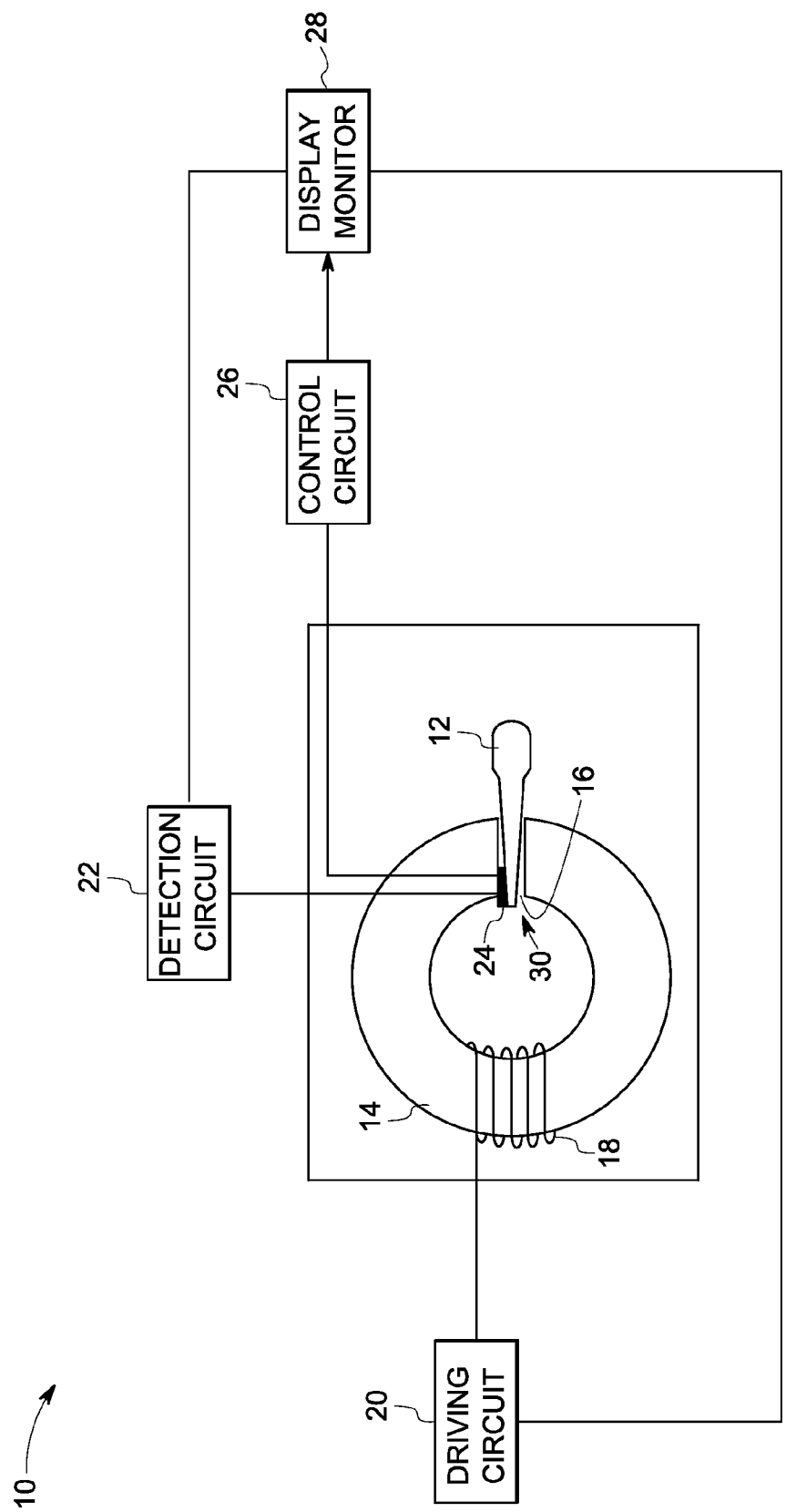
FIG. 1 is a schematic illustration of an exemplary eddy current probe system for inspecting flaws in a part in accordance with an embodiment of the invention.

Turning to the drawings, FIG. 1 is a schematic illustration of an exemplary eddy current probe system 10 for inspecting a part 12 for possible flaws. The eddy current probe system 10 includes a generally C-shaped core 14 having an opening 16 for receiving the part 12. In a particular embodiment, the generally C-shaped core may include a circular C-shaped core. In another embodiment, the generally C-shaped core may include a square C-shaped core. In yet another embodiment, the opening 16 may include a pair of curved sides. A driver coil 18 wrapped around the core 14 creates a magnetic field in the opening 16 via a driving circuit 20. The driving circuit 20 applies a number of excitation signals in the driver coil 18 that induces multiple eddy currents in the part 12. In a particular embodiment, material of the C-shaped core is ferrite that enables focusing the magnetic field that results in a strong magnetic field at an opening of the C-shaped core.

A detection circuit 22 coupled to at least one single element or multiple element eddy current sensor 24 disposed in the opening 16 detects the multiple eddy current signals generated in the part 12. In an exemplary embodiment, the sensor 24 is operable in a differential mode. In another embodiment, the sensor 24 is operable in an absolute mode, in contrast with the differential mode. In yet another embodiment, the sensor 24 can be disposed on one side of the opening or it can be disposed on both sides of the opening. A flaw in the part 12 results in disruption in the eddy current signals that enables detection of the flaw. The driving circuit 20 and the detection circuit 22 may operate with selective frequencies and receive multiple eddy current signals from the detection circuit 22. In a particular embodiment, the system 10 also includes a control circuit 26 that controls a scan of the eddy current sensor 24 and rotation of the part 12. The control circuit 26 enables practice of handheld portable inspection.

It is desirable for the eddy current signal due to the flaws to have a signal-to-noise ratio large enough to be detected in a response signal over background noise. Multi-frequency phase analysis enables achieving such signal-to-noise ratio. Further details of the multi frequency phase analysis may be obtained in U.S. Pat. No. 7,206,706 to Wang et al., entitled "Inspection of Non-planar Parts using Multifrequency Eddy Current with Phase Analysis" and assigned to the same assignee of the present invention, which is hereby incorporated herein by reference. A display monitor 28 may be coupled to the control circuit 26 to display an indication of a presence of at least one flaw in the part 12 based upon the plurality of eddy current signals.

Figure 2:
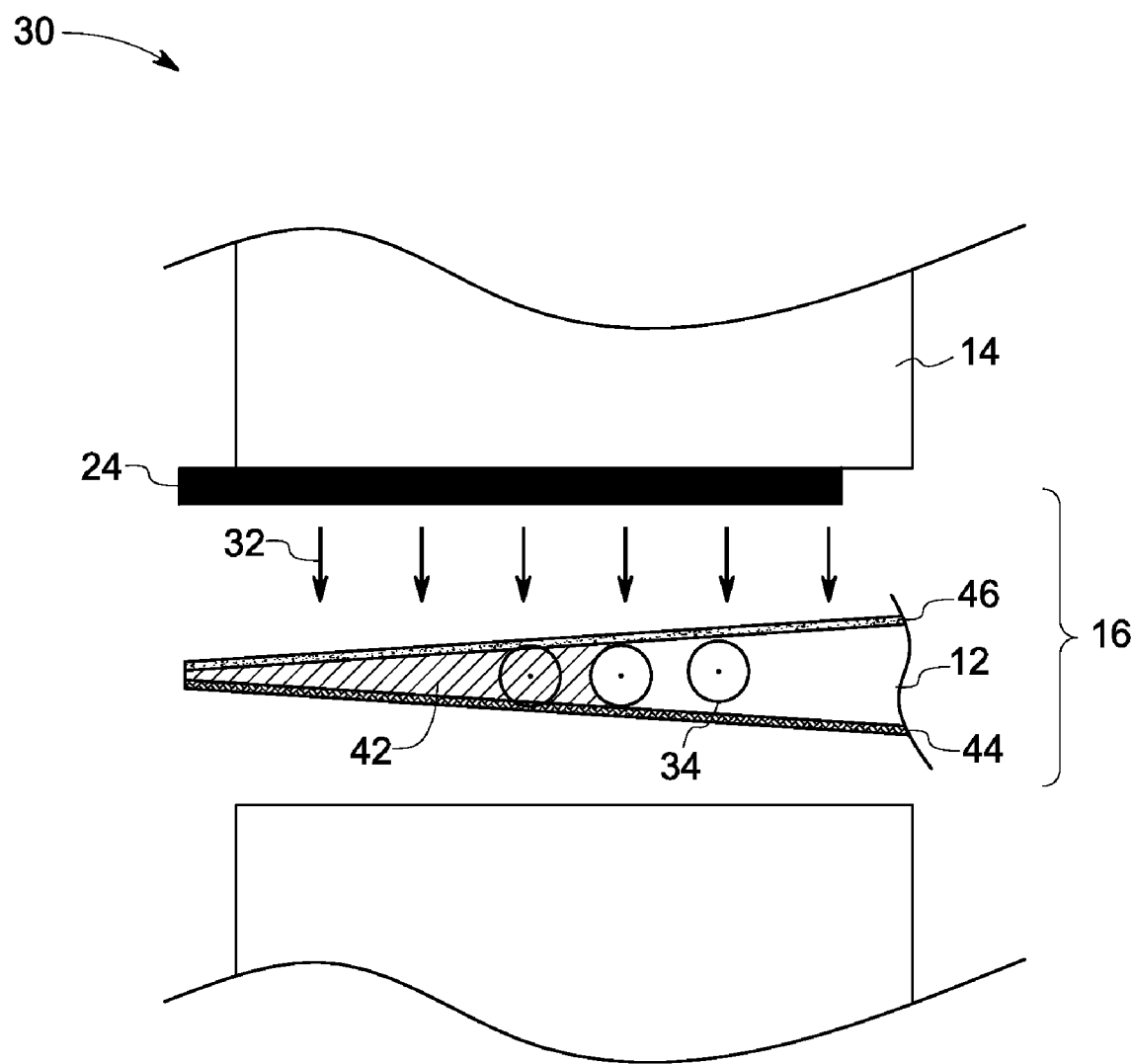
FIG. 2 is a magnified view of the part held in the opening in FIG. 2.

FIG. 2 is a magnified view of the opening 16 with the part 12 as referenced in FIG. 1. When the driver coil 18 is excited by alternating current, it generate alternating (AC) magnetic field 32 at the opening 16. When the part 12 is placed in the opening 16, eddy current flow 34 will be introduced in the part 12. The eddy current sensor 24 detects disruption of the eddy current flow 34. In the illustrated embodiment, the part 12 includes a crack 42. The part 12 also includes a layer of substrate 44 and a coating layer 46. For example, the coating layer 46 may be a conductive coating. In another example, the coating layer 46 may be a nonconductive thermal barrier coating. In one embodiment, the thickness of the coating layer 46 may vary up to about 0.012 inch. A non-limiting example of the substrate 44 includes a nickel-based superalloy. The crack 42 produces a change in the eddy current flow 34 that is detected by the eddy current sensor 24. An adjustment may be performed to obtain an optimal relative position between the eddy current sensor 24 and the part 12.

Figure 3:
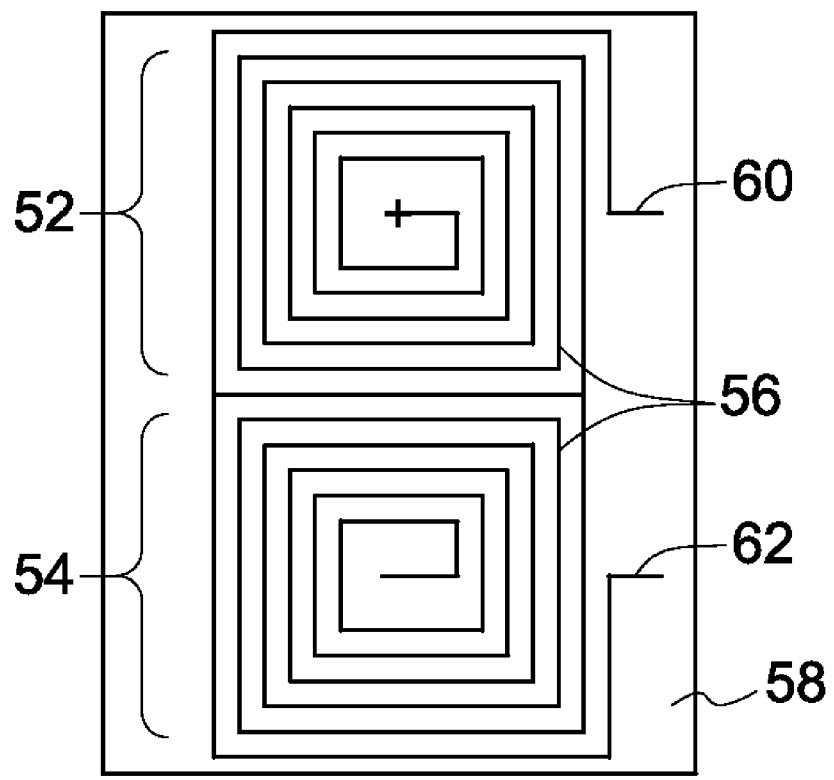
FIG. 3 is a diagrammatical illustration of an exemplary single eddy current sensor employed in the eddy current probe system in FIG. 1.

FIG. 3 is a diagrammatical illustration of an exemplary single eddy current sensor 24 employed in the eddy current probe system in FIG. 1. In the presently contemplated embodiment, the eddy current sensor 24 is a differential single element eddy current array probes (SECAPs) including a positive differential coil 52 and a negative differential coil 54. As used herein, SECAPs refer to single, conducting coils deposited on flexible, dielectric substrates, which is thin and thus allows reduction of the opening 16 for higher sensitivity. The positive differential coil 52 and the negative differential coil 54 include windings 56 wound in a spiral-like pattern and are encapsulated on a flexible substrate 58. In one embodiment, the windings 56 include at least one of copper, silver, or other conductive elements. The substrate 58 may include various materials, such as polyimide dielectric films. In a particular embodiment, the positive differential coil 52 and the negative differential coil 54 include a continuous run of copper windings having an effective diameter of about 2 mm. Further, leads 60 and 62 may be formed on the substrate 58 to provide electrical connection.

Advantageously, the flexible substrate 58 conforms to irregular surfaces of parts and reduces wobble and lift-off of the eddy current sensor 24. In a presently contemplated embodiment, the thickness of the substrate 58 varies between about 25 μm to about 100 μm. In another embodiment, the eddy current sensor 24 may include an absolute SECAP. Further details of the SECAP may be obtained in, U.S. Pat. No. 5,389,876 to Hedengren et al., entitled "Flexible Eddy Current Surface Measurement Array for Detecting Near Surface Flaws in a Conductive Part", and U.S. Pat. No. 6,670,808 to Nath et al., entitled "Self Reference Eddy Current Probe, Measurement System, and Measurement Method" and assigned to the same assignee as the present invention, which is hereby incorporated herein by reference.

Figure 4:
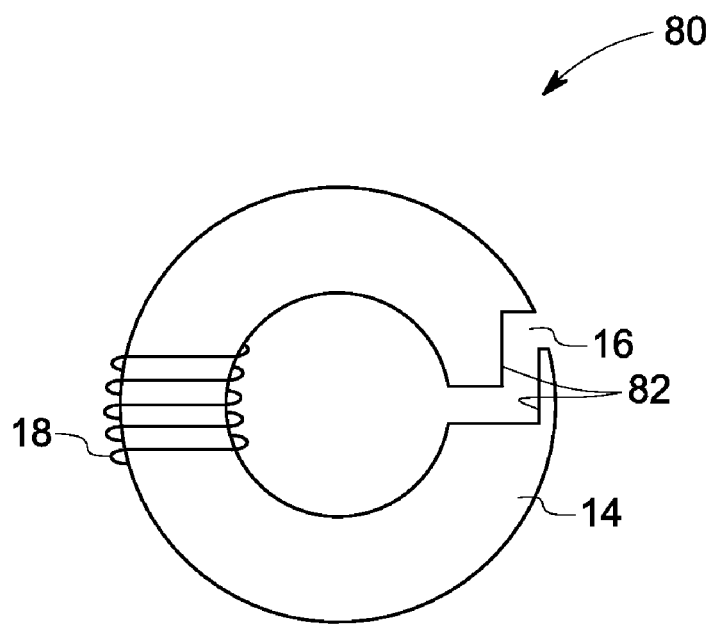
FIG. 4 is a diagrammatic illustration of an alternative configuration of the opening in the eddy current probe system in FIG. 1 in accordance with an embodiment of the invention.

FIG. 4 is a diagrammatic illustration of an alternative configuration 80 of the opening 16 in the eddy current probe system 10 in FIG. 1. In the illustrated embodiment, the opening 16 includes a pair of non-straight sides 82 for irregular shaped tooth.

Figure 5:
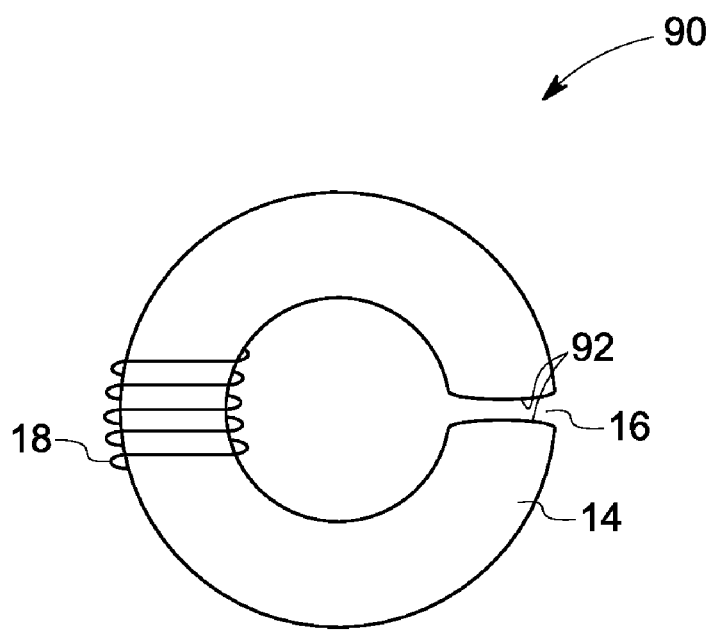
FIG. 5 is a diagrammatic illustration of another alternative configuration of the opening in the eddy current probe system in FIG. 1 in accordance with an embodiment of the invention.

FIG. 5 is a diagrammatic illustration of another alternative configuration 90 of the opening 16 in the eddy current probe system 10 in FIG. 1. In the illustrated embodiment, the opening 16 includes a pair of curved sides 92.

Figure 6:
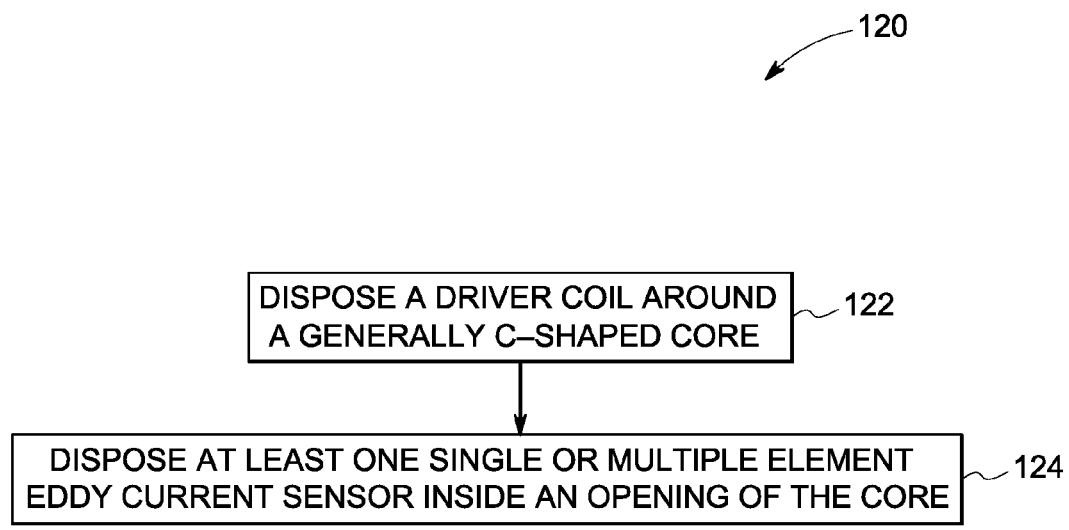
FIG. 6 is a flow chart representing steps in another exemplary method for manufacturing an eddy current probe system in accordance with an embodiment of the invention.

FIG. 6 is a flow chart representing steps in an exemplary method 120 for manufacturing an eddy current probe system. The method 120 includes disposing a driver coil around a generally C-shaped core, as indicated in step 122. At least one single element or multiple element eddy current sensor is disposed inside an opening of the core, as indicated in step 124. In a particular embodiment, the eddy current sensor is attached to a face of the opening with an epoxy or an equivalent adhesive.

The various embodiments of a non-destructive inspection system and method described above thus provide a way to achieve a convenient, efficient and accurate detection of defects or flaws in areas that are not easy to inspect. The system also reduces inspection process time significantly from several hours with stripping FPI process to a few minutes of through-coating inspection, and is therefore very cost-effective. Further, the system and method eliminate labor costs associated with coating stripping and recoating processes, and avoid potential part damage, both of which can result from conventional inspection with stripping.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. Similarly, the various features described, as well as other known equivalents for each feature, can be mixed and matched by one of ordinary skill in this art to construct additional systems and techniques in accordance with principles of this disclosure.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An inspection system for detecting a flaw in a part comprising:
    a generally C-shaped core having an opening for receiving the part;
    a driver coil wrapped around the core for creating a magnetic field in the opening;
    a driving circuit configured to apply a plurality of excitation signals in the driver coil to induce a plurality of eddy current signals in the part;
    at least one single element or multiple element eddy current sensor disposed in the opening, wherein the eddy current sensor is configured to detect a disruption in the plurality of eddy current signals; and
    a control circuit configured to analyze the plurality of eddy current signals by performing a multifrequency phase analysis subsequent to multifrequency mixing of the plurality of eddy current signals, to inspect the part for the presence of the flaw.

2. The inspection system of claim 1, wherein the sensor is operable in an absolute mode.

3. The inspection system of claim 1, wherein the sensor is operable in a differential mode.

4. The inspection system of claim 3, wherein the sensor comprises two generally rectangular coils.

5. The inspection system of claim 1, wherein the generally C-shaped core comprises a circular C-shaped core.

6. The inspection system of claim 1, wherein the generally C-shaped core comprises a ferrite core.

7. The inspection system of claim 1, wherein the opening comprises a pair of curved sides.

8. An inspection system for detecting a flaw in a part comprising:
    a generally C-shaped core having an opening for receiving the part;
    a driver coil wrapped around the core for creating a magnetic field in the opening;
    at least one single element or multiple element eddy current sensor disposed in the opening;
    a driving circuit configured to apply a plurality of excitation signals in the driver coil to induce a plurality of eddy current signals in the part;
    a detection circuit configured to detect a disruption in the plurality of eddy current signals; and
    a control circuit configured to analyze the plurality of eddy current signals by performing a multifrequency phase analysis subsequent to multifrequency mixing of the plurality of eddy current signals, to inspect the part for the presence of the flaw.

9. The inspection system of claim 8, wherein the driving circuit and the detection circuit are further configured to:
    regulate the plurality of excitation signals from the driving circuit at selective frequencies; and
    receive a plurality of eddy current signals from the detection circuit.

10. The inspection system of claim 8, wherein the a control circuit is further configured to control a scan of the eddy current sensor and rotation of the part.

11. The inspection system of claim 8, further comprising a display monitor configured to display an indication of a presence of at least one flaw in the part based upon the plurality of eddy current signals.

12. The inspection system of claim 8, wherein the sensor is operable in an absolute mode.

13. The inspection system of claim 8, wherein the sensor is operable in a differential mode.

14. The inspection system of claim 13, wherein the sensor comprises two generally rectangular coils.

15. The inspection system of claim 8, wherein the generally C-shaped core comprises a circular C-shaped core.

16. The inspection system of claim 8, wherein the generally C-shaped core comprises a ferrite core.

17. The inspection system of claim 8, wherein the opening comprises a pair of curved sides.

18. The inspection system of claim 8, wherein the flaw detected is in a surface or a sub-surface of the part.

19. A method of manufacturing an inspection system comprising:
    disposing a driver coil around a generally C-shaped core;
    coupling a driving circuit to the driver coil, wherein the driving circuit is configured to apply a plurality of excitation signals in the driver coil to induce a plurality of eddy current signals in a part;
    disposing at least one single element or multiple element eddy current sensor inside an opening of the core wherein the eddy current sensor is configured to detect a disruption in the eddy current signals; and
    coupling a control circuit to the at least one single element or multiple element eddy current sensor, wherein the control circuit is configured to analyze the plurality of eddy current signals by performing a multifrequency phase analysis subsequent to multifrequency mixing of the plurality of eddy current signals, to inspect the part for the presence of the flaw.

20. The method of claim 19, wherein the disposing at least one single element or multiple element eddy current sensor comprises attaching the sensor to the core via an adhesive epoxy.

* * * * *